(12) United States Patent
Chen et al.

(10) Patent No.: US 11,919,842 B2
(45) Date of Patent: Mar. 5, 2024

(54) POLYMERCAPTAN COMPOUND AND PREPARATION METHOD THEREOF, CURING AGENT, RESIN COMPOSITION AND USE THEREOF

(71) Applicant: WELDTONE TECHNOLOGY CO., LTD, Fujian (CN)

(72) Inventors: Changjing Chen, Fujian (CN); Tao Liu, Fujian (CN); Hongteng Lin, Fujian (CN); Shuai Li, Fujian (CN)

(73) Assignee: WELDTONE TECHNOLOGY CO., LTD, Fujian (CN)

( * ) Notice: Subject to any disclaimer, the term of this patent is extended or adjusted under 35 U.S.C. 154(b) by 0 days.

(21) Appl. No.: 18/015,721

(22) PCT Filed: Aug. 19, 2022

(86) PCT No.: PCT/CN2022/113624
§ 371 (c)(1),
(2) Date: Jan. 12, 2023

(87) PCT Pub. No.: WO2023/065802
PCT Pub. Date: Apr. 27, 2023

(65) Prior Publication Data
US 2023/0373912 A1 Nov. 23, 2023

(30) Foreign Application Priority Data
Oct. 22, 2021 (CN) .......................... 202111232232.6

(51) Int. Cl.
*C07C 319/02* (2006.01)
*C07C 323/16* (2006.01)
(Continued)

(52) U.S. Cl.
CPC .......... *C07C 323/16* (2013.01); *C07C 319/02* (2013.01); *C08G 59/66* (2013.01);
(Continued)

(58) Field of Classification Search
CPC ..... C07C 323/16; C07C 319/02; C08G 59/66; C08G 59/686; C09J 11/06; C09J 163/00
(Continued)

(56) References Cited

U.S. PATENT DOCUMENTS

| 4,266,055 A | 5/1981 | Inoue et al. |
| 4,721,814 A | 1/1988 | Zahir et al. |

(Continued)

FOREIGN PATENT DOCUMENTS

| CN | 105764907 | 7/2016 |
| CN | 107428781 | 12/2017 |

(Continued)

OTHER PUBLICATIONS

Sebastian Reinelt et al., "Investigations of thiol-modified phenol derivatives for the use in thiol-ene photopolymerizations", Beilstein Journal of Organic Chemistry, Jul. 2014, pp. 1733-1740.
(Continued)

*Primary Examiner* — David T Karst
(74) *Attorney, Agent, or Firm* — JCIPRNET

(57) ABSTRACT

The present disclosure belongs to polymercaptan compounds and application fields thereof, and particularly relates to a polymercaptan compound and a preparation method thereof, a curing agent, a resin composition, an adhesive and a sealant. The polymercaptan compound is represented by formula (I), wherein $R^1$, $R^2$, $R^3$, $R^5$, $R^7$ and $R^8$ are each independently selected from one of a hydrogen atom, an alkyl group with 1-5 carbon atoms and an alkoxy group with 1-5 carbon atoms, $R^4$ and $R^6$ are each independently selected from an alkylene group with 1-5 carbon atoms, and m and n are each independently 0, 1, 2 or 3.

13 Claims, 4 Drawing Sheets

(51) Int. Cl.
*C08G 59/66* (2006.01)
*C08G 59/68* (2006.01)
*C09J 11/06* (2006.01)
*C09J 163/00* (2006.01)

(52) U.S. Cl.
CPC ............ *C08G 59/686* (2013.01); *C09J 11/06* (2013.01); *C09J 163/00* (2013.01)

(58) Field of Classification Search
USPC ........................................................ 528/406
See application file for complete search history.

(56) References Cited

U.S. PATENT DOCUMENTS

| 2017/0007505 A1 | 1/2017 | Mosczner et al. |
| 2019/0202774 A1* | 7/2019 | Gao .................... C07C 43/23 |

FOREIGN PATENT DOCUMENTS

| CN | 111315719 | 6/2020 |
| CN | 113788935 | 12/2021 |
| CN | 113788936 | 12/2021 |
| CN | 113912523 | 1/2022 |
| CN | 113943420 | 1/2022 |
| JP | S56-1J0671 | 9/1981 |
| JP | 2002128827 | 5/2002 |
| JP | 2012122012 | 6/2012 |
| JP | 2015059099 | 3/2015 |
| JP | 2019085408 | 6/2019 |
| JP | 2019214711 | 12/2019 |
| WO | 2018051713 | 3/2018 |

OTHER PUBLICATIONS

Dailyn Guzman et al., "Novel thermal curing of cycloaliphatic resins by thiol-epoxy click process with several multifunctional thiols", Polymer International, Feb. 2017, pp. 1697-1707.

Dailyn Guzman et al., "Preparation of new biobased coatings from a triglycidyl eugenol derivative through thiol-epoxy click reaction", Progress in Organic Coatings, Jan. 2018, pp. 259-267.

Dailyn Guzman et al., "Fully renewable thermosets based on bis-eugenol prepared by thiol-click chemistry", Reactive and Functional Polymers, Mar. 2019, pp. 1-43.

"International Search Report (Form PCT/ISA/210) of PCT/CN2022/113624," dated Oct. 21, 2022, with English translation thereof, pp. 1-9.

"Written Opinion of the International Searching Authority (Form PCT/ISA/237) of PCT/CN2022/113624," dated Oct. 21, 2022, with English translation thereof, pp. 1-8.

* cited by examiner

POLYMERCAPTAN COMPOUND AND PREPARATION METHOD THEREOF, CURING AGENT, RESIN COMPOSITION AND USE THEREOF

CROSS-REFERENCE TO RELATED APPLICATION

This patent application is a 371 of international application of PCT application serial no. PCT/CN2022/113624, filed on Aug. 19, 2022, which claims the benefit and priority of Chinese Patent Application No. 202111232232.6 filed on Oct. 22, 2021, entitled "POLYMERCAPTAN COMPOUND AND PREPARATION METHOD THEREOF, CURING AGENT, RESIN COMPOSITION, ADHESIVE AND SEALANT", the disclosure of which is incorporated by reference herein in its entirety as part of the present application.

TECHNICAL FIELD

The present disclosure belongs to the field of a polymercaptan compounds and uses thereof, in particular to a polymercaptan compound and a preparation method thereof, a curing agent using the polymercaptan compound, a resin composition using the polymercaptan compound and use of the resin composition as an ingredient of an adhesive or a sealant.

RELATED ART

Epoxy resins have excellent property in the aspects of mechanical property, electrical property, heat resistance, chemical resistance, bonding strength and the like, and therefore are widely applied to the fields of coatings, electrical and electronic insulating materials, adhesives and the like. In recent years, a single-component epoxy composition cured by mixing an epoxy resin with a curing agent in advance and heating when in use is developed in addition to a so-called double-component epoxy resin composition cured by mixing the epoxy resin with the curing agent when in use. Especially in recent years, there are increasing demands for flexibility and thinness in the field of electronic circuits, and there are constantly improved requirements on low-temperature curable single-component epoxy resin compositions in order to protect semiconductor elements so that circuits are highly centralized or connection reliability is improved.

A polymercaptan compound with multiple mercapto groups in a molecule have a wide range of uses, for example uses that it serves as a curing agent for epoxy resins and a mercapto-olefin click reaction have been well known. An epoxy resin composition which uses the polymercaptan compound as the curing agent and meanwhile comprises a tertiary amine curing accelerator can be rapidly cured at a relatively low temperature, and can meet the requirements on low-temperature curable single-component epoxy resin compositions. However, most of the currently known polymercaptan curing agents are connected with the mercapto groups through ester bonds, which usually results in the problems of poor moisture resistance and decreased bonding strength in a high humidity environment. Furthermore, trimercaptopropyl isocyanurate synthesized in U.S. Pat. No. 4,266,055A and JPS56120671A has no the ester bond in the molecule, and therefore is used as a curing agent of an epoxy resin composition having excellent water resistance, however, this curing agent can emit malodour (strong sulfur odor) at room temperature, and the cured product is unsatisfactory in heat resistance and has poor toughness. In addition, a mainstream practice in the industry is to use mercaptoalkyl glycolurea as the curing agent of the epoxy resin in order to simultaneously endow the cured epoxy resin with good moisture resistance and heat resistance. For example, patents CN201480064943.9 and JP2015059099A disclose the so-called polymercaptan curing agent of mercaptoalkyl glycolurea. Although this polymercaptan curing agent has good moisture resistance and heat resistance, patents CN201680014880.5 proposes that this polymercaptan curing agent is a solid at room temperature, which easily causes precipitation of crystals when forming a complex with the epoxy resin, so that components therein become heterogeneous, at this moment, another mercaptoethyl glycolurea compound is needed for combination, so as to liquefy the solid polymercaptan curing agent, and finally form a liquid oligomer mixture with a disulfide bond as the curing agent. Although this method can allow the curing agent to be converted into the liquid, the procedures and cost of the reaction are increased. Moreover, the mercaptoalkyl glycolurea curing agent involved in CN201480064943.9 also has the risk of reducing the storage stability of the single-component low-temperature curing epoxy glue.

In summary, the present mercaptan compounds and the curing agents containing the mercaptan compounds mainly have the following problems:

(1) most of the existing polymercaptan curing agents contain ester bonds, which are easy to hydrolyze in a high-temperature high-humidity temperature, thereby reducing the bonding strength of the epoxy adhesive so that bonding is ineffective, and generally have poor heat resistance;

(2) most of the existing polymercaptan curing agents have strong odor, which seriously affects the working environment when sizing;

(3) the existing mercaptoalkyl glycolurea curing agents are solid at room temperature. If they are to become liquid to improve crystal precipitation time, a mercaptoethyl glycolurea compound with a disulfide bond is needed for combination, so there is a need for additional coupling to form the oligomer mixture when in preparation, in such a way, the solid becomes the liquid, which leads to complicated process and high cost. Moreover, the existing mercaptoalkyl glycolurea curing agent can also increase the risk of the storage stability of the single-component low-temperature curing epoxy glue, and is short in working life.

It can be seen from the above analysis that it is urgent to develop an epoxy resin curing agent which is a liquid per se and simultaneously has good moisture resistance, heat resistance, long working life and low odor.

SUMMARY OF INVENTION

The first objective of the present disclosure is to provide a novel polymercaptan compound in order to overcome the defects that the existing polymercaptan curing agent cannot realize that the curing agent is a liquid per se and simultaneously has good moisture resistance, heat resistance, long working life and low odor. The polymercaptan compound is a liquid at room temperature, and can simultaneously have good moisture resistance, heat resistance, long working life and low odor.

The second objective of the present disclosure is to provide a method for preparing the polymercaptan compound described above.

The third objective of the present disclosure is to provide a curing agent which at least comprises the above polymercaptan compound described above.

The fourth objective of the present disclosure is to provide a resin composition which uses the curing agent described above.

The fifth objective of the present disclosure is to provide the use of the resin composition described above as an ingredient of an adhesive or a sealant.

Particularly, the polymercaptan compound provided by the present disclosure is represented by formula (I):

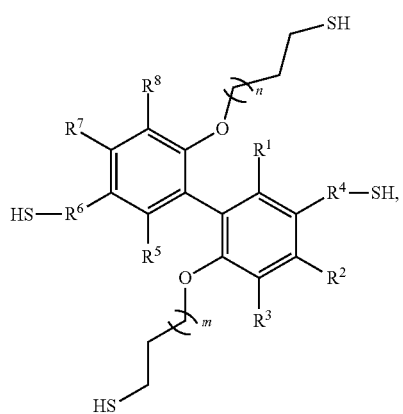

(I)

in the formula (I), $R^1$, $R^2$, $R^3$, $R^5$, $R^7$ and $R^8$ are each independently selected from one of a hydrogen atom, an alkyl group with 1-5 carbon atoms and an alkoxy group with 1-5 carbon atoms, $R^4$ and $R^6$ are each independently selected from an alkylene group with 1-5 carbon atoms, and m and n are each independently 0, 1, 2 or 3.

In a preferred embodiment, in the formula (I), $R^1$, $R^2$, $R^5$ and $R^7$ are all hydrogen atoms, $R^3$ and $R^8$ are each independently selected from a hydrogen atom or a methoxy group, $R^4$ and $R^6$ are each independently selected from an alkylene group with 3-5 carbon atoms, and m and n are 1.

In a preferred embodiment, the polymercaptan compound is selected from at least one of 5,5'-bis(3-mercaptopropyl)-2,2'-bis(3-mercaptobutoxy)biphenyl, 5,5'-bis(3-mercaptopropyl)-2,2'-bis(3-mercaptobutoxy)-3,3'-dimethoxybiphenyl, 5,5'-bis(3-mercaptopropyl)-2,2'-bis(3-mercaptopentoxy)biphenyl, 5,5'-bis(3-mercaptopropyl)-2,2'-bis(3-mercaptopentoxy)-3,3'-dimethoxybiphenyl, 5,5'-bis(3-mercaptopropyl)-2,2'-bis(3-mercaptopropoxy)biphenyl and 5,5'-bis(3-mercaptopropyl)-2,2'-bis(3-mercaptopropoxy)-3,3'-dimethoxybiphenyl.

In a preferred embodiment, a method for preparing the polymercaptan provided by the present disclosure comprising the following steps:

step 1: performing substitution reaction on a phenol compound represented by formula (II) and a first compound represented by formula (III) in the presence of a phase transfer catalyst and under the alkaline condition, and purifying to obtain a first intermediate product as a colorless or faint yellow liquid;

step 2: performing radical addition reaction on the first intermediate product and thioacetic acid in the presence of a radical initiator, and purifying to obtain a second intermediate product as a colorless or faint yellow liquid; and step 3: performing hydrolysis reaction on the second intermediate, and purifying to obtain a product as a colorless or faint yellow thick liquid, i.e., the polymercaptan compound;

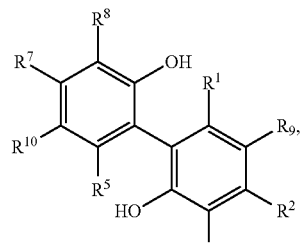

Formula (II)

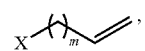

Formula (III)

in the formula (II), $R^1$, $R^2$, $R^3$, $R^5$, $R^7$ and $R^8$ are each independently selected from one of a hydrogen atom, a lower alkyl group with 1-5 carbon atoms and an alkoxy group with 1-5 carbon atoms, and $R^9$ and $R^{10}$ are each independently selected from a 1-alkenylalkyl group with 1-5 carbon atoms;

in the formula (III), X represents chlorine or bromine, and m is 0, 1, 2 or 3.

In a preferred embodiment, in step 1, the substitution reaction is that the phenol compound represented by formula (II) is dissolved into an organic solvent, an alkali is added to provide an alkaline condition, the phase transfer catalyst is added, then above mixture is heated to 40-100° C. under the protection of an inert gas and stirred for 10-60 min, subsequently the first compound represented by formula (III) is added to react for 4-12 h, then a reaction solution is filtered, filtrate is distilled at reduced pressure to remove a solvent, washed with water three times and extracted with trichloromethane, and an organic phase is collected and evaporated to obtain the first intermediate product as the colorless or faint yellow liquid.

In a preferred embodiment, in step 2, the radical addition reaction is that the first intermediate product is dissolved into the organic solvent, the radical initiator is added, above mixture is heated to 40-100° C. under the protection of an inert gas, thioacetic acid is slowly added to perform radical addition reaction for 4-12 h, and then the solvent is removed by distilling at reduced pressure to obtain the second intermediate product as the colorless or faint yellow liquid.

In a preferred embodiment, in step 3, the hydrolysis reaction is that the second intermediate product was dissolved into the organic solvent, hydrochloric acid or sodium hydroxide is added, above mixture is heated to 50-100° C. to react for 3-12 h, the solvent is removed by distilling at reduced pressure, a product obtained after distillation is washed with a 2-8% sodium bicarbonate solution twice and extracted with trichloromethane, and organic phase is collected and then evaporated to obtain the product as the colorless or faint yellow thick liquid, i.e., the polymercaptan compound.

The present disclosure also provides a curing agent, wherein the curing agent at least comprises the polymercaptan compound described above.

The present disclosure also provides a resin compound, wherein the resin compound at least comprises the curing agent described above and a resin, the resin is an alkene compound and/or epoxy resin having a carbon-carbon double bond in the molecule.

In a preferred embodiment of the present disclosure, when the resin is the epoxy resin, the resin composition comprises an amine as a curing accelerator.

In a preferred embodiment of the present disclosure, when the resin is the epoxy resin, the resin composition comprises a reaction product of the epoxy resin and the amine as the curing accelerator.

In a preferred embodiment of the present disclosure, when the resin is the epoxy resin, the resin composition comprises a reaction product of a compound with more than one isocyanate group in the molecule and a compound with at least one of a primary amino group and a secondary amino group in the molecule as the curing accelerator.

The present disclosure also provides use of the resin composition described above as an ingredient of an adhesive or a sealant.

The present disclosure has the beneficial effects:

(1) the polymercaptan compound provided by the present disclosure has good moisture resistance and heat resistance;

(2) the polymercaptan compound provided by the present disclosure has low odor;

(3) the polymercaptan compound provided by the present disclosure is a liquid at room temperature, can be directly used as the curing agent for curing the resin composition without additional coupling to form an oligomeric mixture and combination with other polymercaptan compounds and has low cost, and the resin composition can be used as the component of the sealant and the adhesive. In addition, the polymercaptan compound can improve the storage stability of the single-component low-temperature curing epoxy resin, and has long working life and wide application prospect.

DESCRIPTION OF EMBODIMENTS

Figure 1:
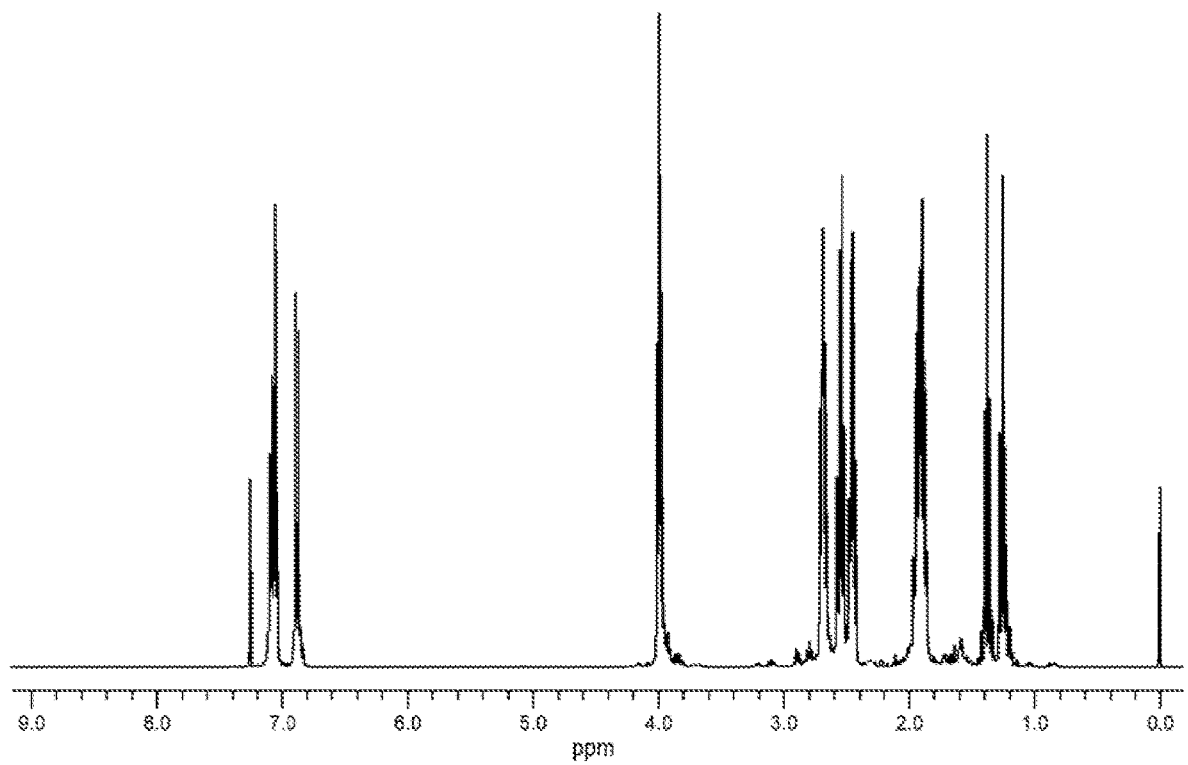
FIG. 1 is a hydrogen nucilar magnetic resonance ($^1$H-NMR) image of 5,5'-bis(3-mercaptopropyl)-2,2'-bis(3-mercaptopropoxy) biphenyl obtained in example 1.

Particularly, the polymercaptan compound provided by the present disclosure is represented by formula (I):

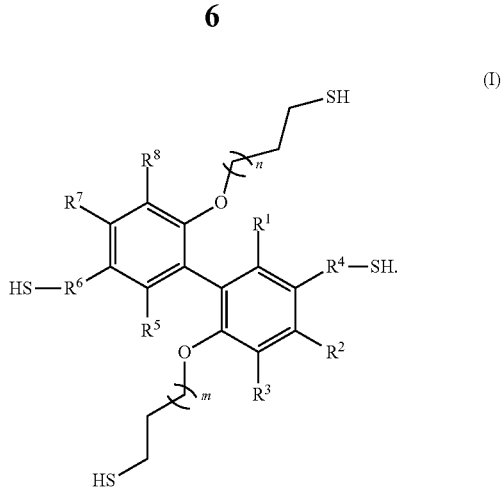

In formula (I), $R^1$, $R^2$, $R^3$, $R^5$, $R^7$ and $R^8$ are each independently selected from one of a hydrogen atom, an alkyl group with 1-5 carbon atoms and an alkoxy group with 1-5 carbon atoms, $R^4$ and $R^6$ are each independently selected from an alkylene group with 1-5 carbon atoms, and m and n are each independently 0, 1, 2 or 3. Wherein, specific examples of the alkyl group with 1-5 carbon atoms include but are not limited to methyl, ethyl, n-propyl, isopropyl, n-butyl, sec-butyl, isobutyl, tert-butyl, n-pentyl, isopentyl, tert-pentyl or neopentyl. Specific examples of the alkoxy group with 1-5 carbon atoms include but are not limited to methoxy, ethoxy, propoxy, isopropoxy, butoxy or isobutoxy. Specific examples of the alkylene group with 1-5 carbon atoms include but are not limited to methylene, ethylidene, n-propylidene, isopropylidene, n-butylene, sec-butylene, isobutylene, ter-butylene, n-pentylene, isopentylene, tert-pentylene or neopentylene.

In a preferred embodiment of the present disclosure, in formula (I), $R^1$, $R^2$, $R^5$ and $R^7$ are all hydrogen atoms; $R^3$ and $R^8$ are each independently selected from a hydrogen atom or a methoxy group; $R^4$ and $R^6$ are each independently selected from an alkylene group with 3-5 carbon atoms, such as n-propylidene, isopropylidene, n-butylene, sec-butylene, isobutylene, ter-butylene, n-pentylene, isopentylene, tert-pentylene or neopentylene; m and n are 1.

Specific examples of the polymercaptan compound include but are not limited to at least one of 5,5'-bis(3-mercaptopropyl)-2,2'-bis(3-mercaptobutoxy)biphenyl ($R^1$, $R^2$, $R^3$, $R^5$, $R^7$ and $R^8$ are all hydrogen atoms, $R^4$ and $R^6$ are both alkylene groups with 3 carbon atoms, and m and n are both 2), 5,5'-bis(3-mercaptopropyl)-2,2'-bis(3-mercaptobutoxy)-3,3'-dimethoxybiphenyl ($R^1$, $R^2$, $R^5$ and $R^7$ are all hydrogen atoms, $R^3$ and $R^8$ are each independently selected from a methoxy group, $R^4$ and $R^6$ are both alkylene groups with 3 carbon atoms, and m and n are both 2), 5,5'-bis(3-mercaptopropyl)-2,2'-bis(3-mercaptopentoxy)biphenyl ($R^1$, $R^2$, $R^3$, $R^5$, $R^7$ and $R^8$ are all hydrogen atoms, $R^4$ and $R^6$ are alkylene groups with 3 carbon atoms, and m and n are both 3), 5,5'-bis(3-mercaptopropyl)-2,2'-bis(3-mercaptopentoxy)-3,3'-dimethoxybiphenyl ($R^1$, $R^2$, $R^3$, $R^5$ and $R^7$ are all hydrogen atoms, $R^3$ and $R^8$ are each independently selected from a methoxy group, $R^4$ and $R^6$ are both alkylene groups with 3 carbon atoms, and m and n are both 3), 5,5'-bis(3-mercaptopropyl)-2,2'-bis(3-mercaptopropoxy)biphenyl ($R^1$, $R^2$, $R^3$, $R^5$, $R^7$ and $R^8$ are all hydrogen atoms, $R^4$ and $R^6$ are both alkylene groups with 3 carbon atoms, and m and n are both 1) and 5,5'-bis(3-mercaptopropyl)-2,2'-bis(3-mercaptopropoxy)-3,3'-dimethoxybiphenyl ($R^1$, $R^2$, $R^5$ and $R^7$ are all hydrogen atoms, $R^3$ and $R^8$ are each independently selected from a methoxy group, $R^4$ and $R^6$ are both alkylene groups with 3 carbon atoms, m and n are both 1).

The preparation method of the polymercaptan compound provided by the present disclosure comprises the following steps:
- step 1: performing substitution reaction on a phenol compound represented by formula (II) and a first compound represented by formula (III) in the presence of a phase transfer catalyst and under the alkaline condition, and purifying to obtain a first intermediate product as a colorless or faint yellow liquid;
- step 2: performing radical addition reaction on the first intermediate product and thioacetic acid in the presence of a radical initiator, and purifying to obtain a second intermediate product as a colorless or faint yellow liquid;
- step 3: performing hydrolysis reaction on the second intermediate, and purifying to obtain a product as a colorless or faint yellow thick liquid, i.e., the polymercaptan compound,

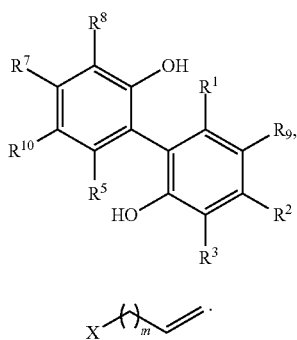

Formula (II)

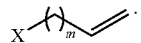

Formula (III)

In the formula (II), $R^1$, $R^2$, $R^3$, $R^5$, $R^7$ and $R^8$ are each independently selected from one of a hydrogen atom, a lower alkyl group with 1-5 carbon atoms and an alkoxy group with 1-5 carbon atoms; preferably, $R^1$, $R^2$, $R^5$ and $R^7$ are all hydrogen atoms, and $R^3$ and $R^8$ are each independently selected from a hydrogen atom or a methoxy group; $R^9$ and $R^{10}$ are each independently selected from 1-alkenyl-alkyl group with 1-5 carbon atoms, preferably a 1-alkenyl-alkyl group with 3-5 carbon atoms.

In the formula (III), X represents chlorine or bromine, and m is 0, 1, 2 or 3.

In step 1, the substitution reaction is preferably that a phenol compound represented by formula (II) is dissolved into an organic solvent, an alkali is added to provide an alkaline condition, a phase transfer catalyst is added, then above mixture is heated to 40-100° C. under the protection of an inert gas and stirred for 10-60 min, subsequently a first compound represented by formula (III) is added to react for 4-12 h, then the reaction solution is filtered, filtrate is distilled at reduced pressure to remove the solvent, washed with water three times and extracted with trichloromethane, an organic phase is collected and then evaporated to obtain the first intermediate product as the colorless or faint yellow liquid.

The types of alkali are not specifically limited and can be conventional selections in the art, and specific examples of alkali include but are not limited to at least one of potassium carbonate, sodium carbonate, sodium hydroxide, potassium hydroxide, triethylamine and p-dimethylaminopyridine.

The phase transfer catalysts can be various existing substances that can catalyze the substitution reaction between a phenolic hydroxyl group in the phenol compound represented by formula (II) and chlorine or bromine in the first compound represented by formula (III), preferably at least one of cyclic crown ethers, polyethers and ammonium. Wherein, specific examples of the cyclic crown ethers include but are not limited to at least one of 18-crown-6, 15-crown-5 and cyclodextrin. Specific examples of the polyethers include but are not limited to chain polyethylene glycol and/or chain polyethylene glycol dialkyl ether. Specific examples of the ammonium include but are not limited at least one of benzyltriethyl ammonium chloride, tetrabutyl ammonium bromide, tetrabutyl ammonium chloride, tetrabutyl ammonium bisulfate, trioctylmethyl ammonium chloride, dodecyltrimethyl ammonium chloride and tetradecyltrimethyl ammonium chloride.

In step 2, the radical addition reaction is preferably that the first intermediate product is dissolved into an organic solvent, a radical initiator is added, above mixture is heated to 40-100° C. under the protection of an inert gas, thioacetic acid is slowly added, radical addition reaction is performed for 4-12 h, and then the solvent is removed by distilling at reduced pressure to obtain the second intermediate product as the colorless or faint yellow liquid.

The radical initiators can be various existing substances that can initiate the radical addition reaction between a double bond in the first intermediate and the mercapto group in thioacetic acid, and can be azo initiators and/or peroxide initiators. Wherein, specific examples of the azo initiators include but are not limited to at least one of azodiisobutyronitrile, 2,2'-azobis(2-methylbutyronitrile), dimethyl 2,2'-azobis(2-methylpropionate), 2,2-azobisisobutyric acid dimethyl ester, 2,2'-azobis(2-methylpropionamidine) dihydrochloride, azodicarbonamide, 2,2'-azobis[2-(2-imidazolin-2-yl)propane] dihydrochloride, 2-(1-cyano-1-methylethyl)azocarboxamide, 1,1'-azobis(cyanocyclohexane), 4,4'-azobis(4-cyanovaleric acid), 2,2'-azobis[2-(2-imidazolin-2-yl)propane], 2,2'-azodi(2-methylbutyronitrile) and 2,2'-azobis(2,4-dimethyl)valeronitrile. Specific examples of the peroxide initiators include but are not limited to at least one of tert-hexylperoxyisopropyl monocarbonate, tert-hexylperoxy 2-ethyl hexanoate, 1,1,3,3-tetramethylbutylperoxy-2-ethyl hexanoate, tert-butyl peroxypivalate, tert-hexyl peroxypivalate, tert-butyl peroxy neodecanoate, tert-hexyl peroxy neodecanoate, 1,1,3,3-tetramethylbutyl peroxyneodecanoate, 1,1-bis(tert-hexylperoxy)cyclohexane, benzoyl peroxide, 3,5,5-trimethylhexanoyl peroxide, lauroyl peroxide and tert-butylbenzoyl peroxide. From the perspective of raw material availability, the radical initiator is preferably at least one of azodiisobutyronitrile, 2,2'-azobis(2-methylbutyronitrile), dimethyl 2,2'-azobis(2-methylpropionate), tert-hexylperoxyisopropyl monocarbonate, tert-hexylperoxy 2-ethyl hexanoate, 1,1,3,3-tetramethylbutylperoxy-2-ethyl hexanoate, tert-butyl peroxypivalate, tert-hexyl peroxypivalate, tert-butyl peroxyneodecanoate, tert-hexyl peroxy neodecanoate, 1,1,3,3-tetramethylbutyl peroxyneodecanoate, 1,1-bis(tert-hexylperoxy)cyclohexane, benzoyl peroxide, 3,5,5-trimethylhexanoyl peroxide, lauroyl peroxide.

In step 3, the hydrolysis reaction is preferably that the second intermediate product is dissolved into alcohol, hydrochloric acid or sodium hydroxide is added, the above mixture is heated to 50-100° C. for 3-12 h, the solvent is removed by distilling at reduced pressure, the product after distillation is washed with a 2-8% sodium carbonate solution twice and extracted with trichloromethane, and the organic phase is collected and evaporated to obtain the product as the colorless or faint yellow thick liquid, i.e., the polymercaptan compound.

In a preferred embodiment of the present disclosure, the substitution reaction in step 1 is performed in the presence of organic solvent I, the radical addition reaction in step 2 is performed in the presence of organic solvent II, and the hydrolysis reaction in step 3 is performed in the presence of organic solvent III. The organic solvent I and the organic solvent II are each preferably and independently selected at least one of methanol, ethanol, propanol, butanol, isopropanol, ethyl acetate, propyl acetate, butyl acetate, tetrahydrofuran, dioxane, acetonitrile, toluene, xylene, dichloromethane, chloroform, carbon tetrachloride, dimethylformamide, dimethylacetamide and dimethyl sulfoxide, respectively. The organic solvent III is preferably alcohol, more preferably unit alcohol with 1-5 carbon atoms, such as at least one of methanol, ethanol, propanol and n-butanol.

The present disclosure also provides a curing agent, wherein the curing agent at least comprises the polymercaptan compound described above.

The present disclosure also provides a resin compound, wherein the resin compound at least comprises the curing agent described above and a resin, the resin is an alkene compound and/or epoxy resin having a carbon-carbon double bond in the molecule.

In a preferred embodiment of the present disclosure, when the resin is the epoxy resin, the resin composition comprises an amine as a curing accelerator.

In a preferred embodiment of the present disclosure, when the resin is the epoxy resin, the resin composition comprises a reaction product of the epoxy resin and the amine as the curing accelerator.

In a preferred embodiment of the present disclosure, when the resin is the epoxy resin, the resin composition comprises a reaction product of a compound with more than one isocyanate group in the molecule and a compound with at least one of a primary amino group and a secondary amino group in the molecule as the curing accelerator.

The present disclosure also provides use of the resin composition described above as an ingredient of an adhesive or a sealant.

The present disclosure will be described in combination with examples.

In the following examples and comparative examples: magnolol is derived from Thain Chemical Technology (Shanghai) Co., Ltd. with the brand of E100338; the phase transfer catalyst 18-crown-6 is derived from Shanghai Titan Technology Co., Ltd., with the brand of 30243D; tetrabutylammonium bromide is derived from Shanghai Titan Technology Co., Ltd. with the brand of 28296F; allyl bromide is derived from Shanghai Titan Technology Co., Ltd. with the brand of 13125C; azodiisobutyronitrile (called "AIBN" for short) is derived from Shanghai McLean Biochemical Technology Co., Ltd., with the brand name of A800353; benzoyl peroxide is derived from Shanghai McLean Biochemical Technology Co., Ltd., with the brand of B802244; thioacetic acid is derived from Sinopharm Chemical Reagent Co., Ltd., with the brand of 80128126; 5,5'-diallyl-3,3'-dimethoxy-2,2'-biphenol is derived from Thain Chemical Technology (Shanghai) Co., Ltd. with the brand of D050881; allyl chloride is derived from Thain Chemical Technology (Shanghai) Co., Ltd. with the brand of W310002; 5-bromo-1-pentene is derived from Thain Chemical Technology (Shanghai) Co., Ltd. with the brand of W330079; the latent curing accelerator is derived from Ajikure Fine Chemicals Co., Ltd., with the brand of AJICURE PN-23; the photoinitiator is derived from Eigenmont, the brand of 2,2-dimethoxy-2-phenyl phenylethanone is Omnirad 651, the brand of 2-hydroxy-2-methylpropiophenone is Omnirad 1173, and the brand of diphenyl-(2,4,6-trimethylbenzoyl) oxyphosphorus is Omnirad TPO; 1,3,4,6-tetra(2-mercaptoethyl) glycolurea is derived from Siguo Chemical Industry Co., Ltd., with the trade name of TS-G, which has a structure shown in formula (IV); 1,1-(dithiodiethylenediyl)-bis[3,4,6-tris(2-mercaptoethyl)glycolurea] is derived from Siguo Chemical Industry Co., Ltd., which has a structure shown in formula (V); the bisphenol A epoxy resin is derived from jER-828EL of Mitsubishi Chemical Co., Ltd; the hydrogenated bisphenol A epoxy resin is derived from Epalloy 5000 of CVC Thermosetting Special Materials Company of the United States; the alkene compound with the carbon-carbon double bond in the molecule is derived from tricyclodecane dimethanol diacrylate SR833S from Sadoma Chemical Co., Ltd., and bisphenol A epoxy diacrylate EBECRYL600 from Zhanxin Resin (China) Co., Ltd; the polymerization inhibitor p-hydroxyanisole is derived from MEHQ of Solvay Company; the stabilizer triethyl borate is derived from B0520 from TCI Company of Japan; the polymercaptan curing agent with the ester bond: pentaerythritol tetra (3-mercaptopropionic acid) ester is derived from PEMP of SC Organic Chemical Co., Ltd,

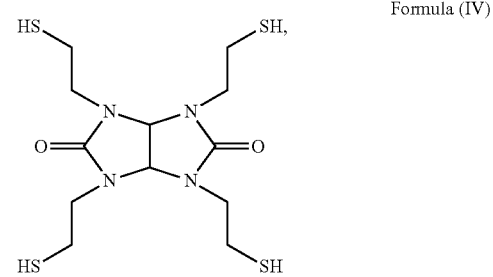

Formula (IV)

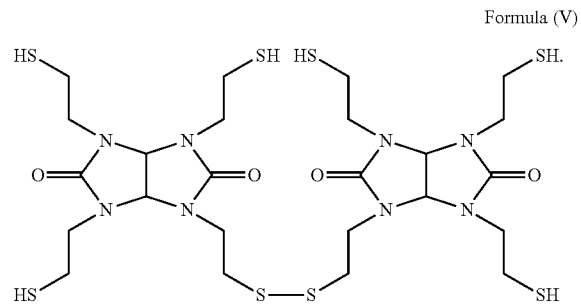

Formula (V)

Example 1

This example is used for illustrating the preparation of the polymercaptan compound (5,5'-bis(3-mercaptopropyl)-2,2'-bis(3-mercaptopropoxy)biphenyl) provided by the present disclosure. Specific steps and a reaction flowchart are as follows:

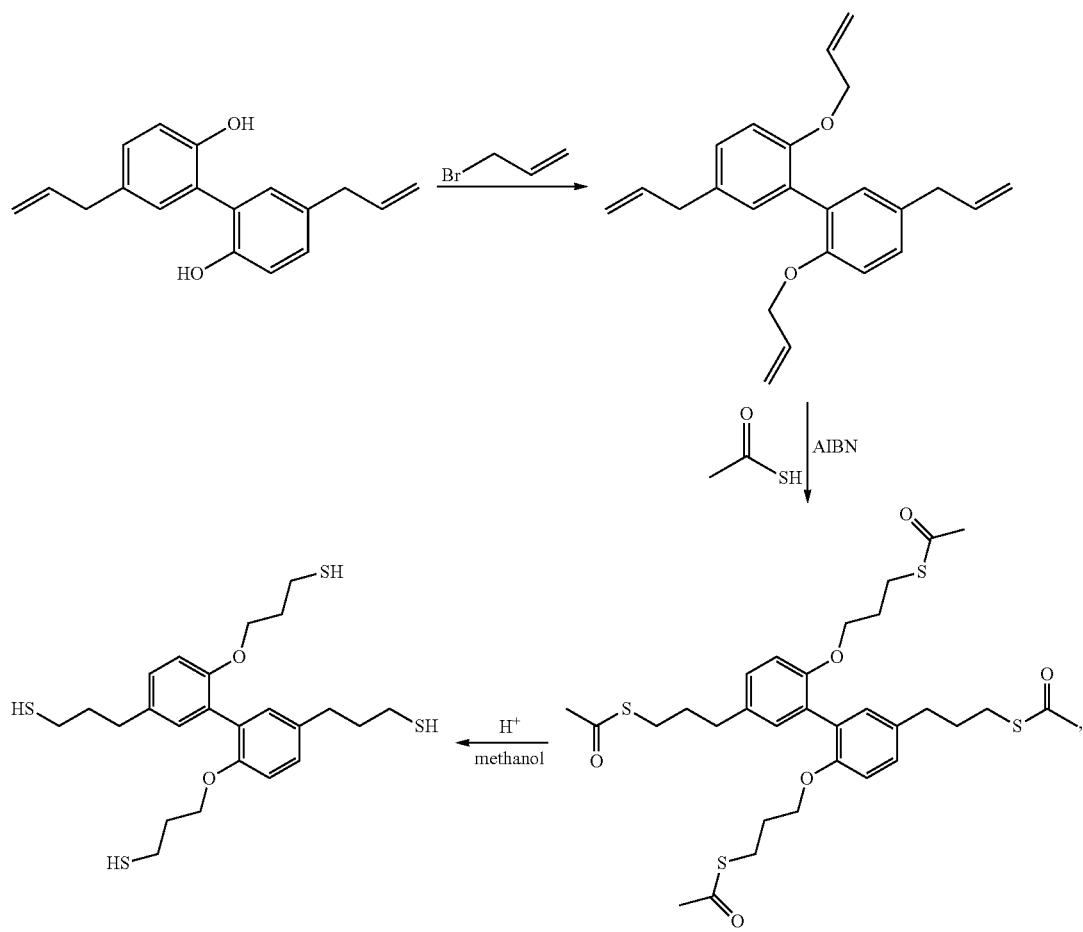

step 1: 80 g of magnolol was dissolved into 200 mL of acetone, 103.6 g of potassium carbonate and 7.9 g of phase transfer catalyst 18-crown-6 were added, the above mixture was heated to 70° C. under the protection of an inert gas and stirred for 10 min, then 79.8 g of allyl bromide was slowly added to react for 8, then the reaction solution was filtered, the filtrate was distilled at reduced pressure to remove the solvent, washed with water three times and extracted with trichloromethane, and an organic phase was collected and then evaporated to dryness, so as to obtain a first intermediate product as a faint yellow liquid;

step 2: the first intermediate product obtained in step 1 was dissolved into 200 mL of tetrahydrofuran, 5.4 g of radical initiator azodiisobutyronitrile was added, the above mixture was heated to 70° C. under the protection of an inert gas, 96.2 g of thioacetic acid was slowly added, the solvent and excessive thioacetic acid were removed by distilling at reduced pressure after reacting for 12 h, so as to obtain a second intermediate product as a faint yellow liquid;

step 3: the second intermediate product obtained in step 2 was dissolved into 300 mL of methanol, 60 mL of hydrochloric acid for hydrolysis, the above mixture was heated to 60° C. to perform hydrolysis reaction for 12 h, the solvent was removed by distilling at reduced pressure, the product after distillation was washed with 5% sodium bicarbonate twice and extracted with trichloromethane, and the organic phase was collected and evaporated, so as to obtain 124. 8 g of final product as a faint yellow thick liquid, i.e., 5,5'-bis(3-mercaptopropyl)-2,2'-bis(3-mercaptopropoxy)biphenyl, with a total yield of 86.2%. The 5,5'-bis(3-mercaptopropyl)-2,2'-bis(3-mercaptopropoxy)biphenyl substantially has no sulfur odor.

Figure 2:
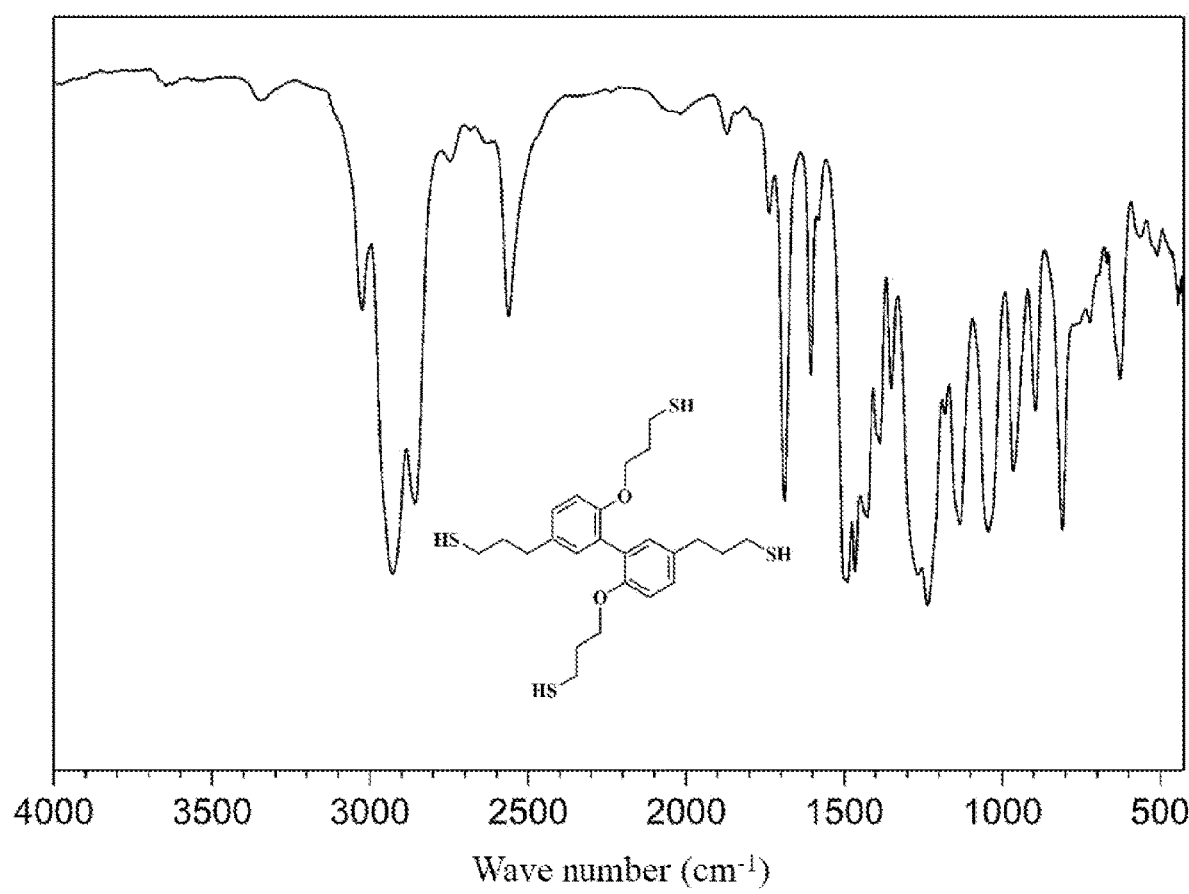
FIG. 2 is an infrared radiation (IR) spectrogram of 5,5'-bis(3-mercaptopropyl)-2,2'-bis(3-mercaptopropoxy) biphenyl obtained in example 1.

The $^1$H-NMR image and IR spectrogram of the 5,5'-bis(3-mercaptopropyl)-2,2'-bis(3-mercaptopropoxy)biphenyl are shown in FIG. 1 and FIG. 2. It can be seen from FIG. 1 that the proton peak on the biphenyl ring is near the chemical shift 7.0 ppm, the peaks at the chemical shifts 4.0 ppm, 2.6 ppm and 1.95 ppm correspond to the alkoxy groups on the biphenyl ring, the peaks at the chemical shifts 2.7 ppm, 2.5 ppm and 1.89 ppm correspond to the alkyl groups on the biphenyl ring, and the peaks at the chemical shifts 1.42 ppm and 1.3 ppm respectively correspond to the alkyl mercapto group and alkoxy mercapto group on the biphenyl ring. It can be seen from FIG. 2 that an absorption peak on the biphenyl ring is at 1492 cm$^{-1}$, 815 cm$^{-1}$ corresponds to the Ar—H bending vibration on the biphenyl ring, a C—H stretching vibration absorption peak on the alkyl chain is at 2928 cm$^{-1}$, an absorption peak occurring at 1246 cm$^{-1}$ is alkoxy C—O stretching vibration, and an absorption peak at 2560 cm$^{-1}$ corresponds to the mercapto group. Accordingly, the 5,5'-bis(3-mercaptopropyl)-2,2'-bis(3-mercaptoprooxy)biphenyl has a structure shown in formula (I), wherein R$^1$, $R^2$, $R^3$, $R^5$, $R^7$ and $R^8$ are all hydrogen atoms, $R^4$ and $R^6$ are both alkylene groups with 3 carbon atoms, and m and n are both 1.

Example 2

This example is used for illustrating the preparation of the polymercaptan compound 5,5'-bis(3-mercaptopropyl)-2,2'-bis(3-mercaptopropoxy)-3,3'-dimethoxybiphenyl), specifically comprising the following steps:

step 1: 98 g of 5,5'-diallyl-3,3'-dimethoxy-2,2'-diphenol were dissolved into 250 mL of acetone, 103.6 g of potassium carbonate and 7.9 g of phase transfer catalyst 18-crown-6 were added, the above mixture was heated to 70° C. under the protection of nitrogen and stirred for 10 min, then 79.8 g of allyl bromide was slowly added, the reaction solution was filtered after 8 h of reaction, the filtrate was distilled at reduced pressure to remove the solvent, washed with water three times and extracted with trichloromethane, and the organic phase was collected and evaporated to obtain a first intermediate product as a faint yellow liquid;

step 2: the first intermediate product obtained in step 1 was dissolved into 200 mL of tetrahydrofuran, 5.4 g of radical initiator azodiisobutyronitrile, the above mixture was heated to 70° C. under the protection of an inert gas, 96.2 g of thioacetic acid was slowly added, and the solvent was removed by distillation at reduced pressure after 12 h of reaction to obtain a second intermediate product as a faint yellow liquid;

step 3: the second intermediate product obtained in step 2 was dissolved into 300 mL of methanol, 60 mL of hydrochloric acid was added for hydrolysis, the above mixture was heated to 70° C. to be subjected to hydrolysis reaction for 12 h, the solvent was removed by distillation at reduced pressure, the product after distillation was washed with a 5% sodium dicarbonate solution twice and extracted with trichloromethane, and the organic phase was collected and evaporated to obtain 137.7 g of final product as a faint yellow thick liquid, i.e., 5,5'-bis(3-mercaptopropyl)-2,2'-bis(3-mercaptopropoxy)-3,3'-dimethoxybiphenyl, with a total yield of 84.5%. The 5,5'-bis(3-mercaptopropyl)-2,2'-bis(3-mercaptopropoxy)-3,3'-dimethoxybiphenyl substantially has no sulfur odor.

Figure 3:
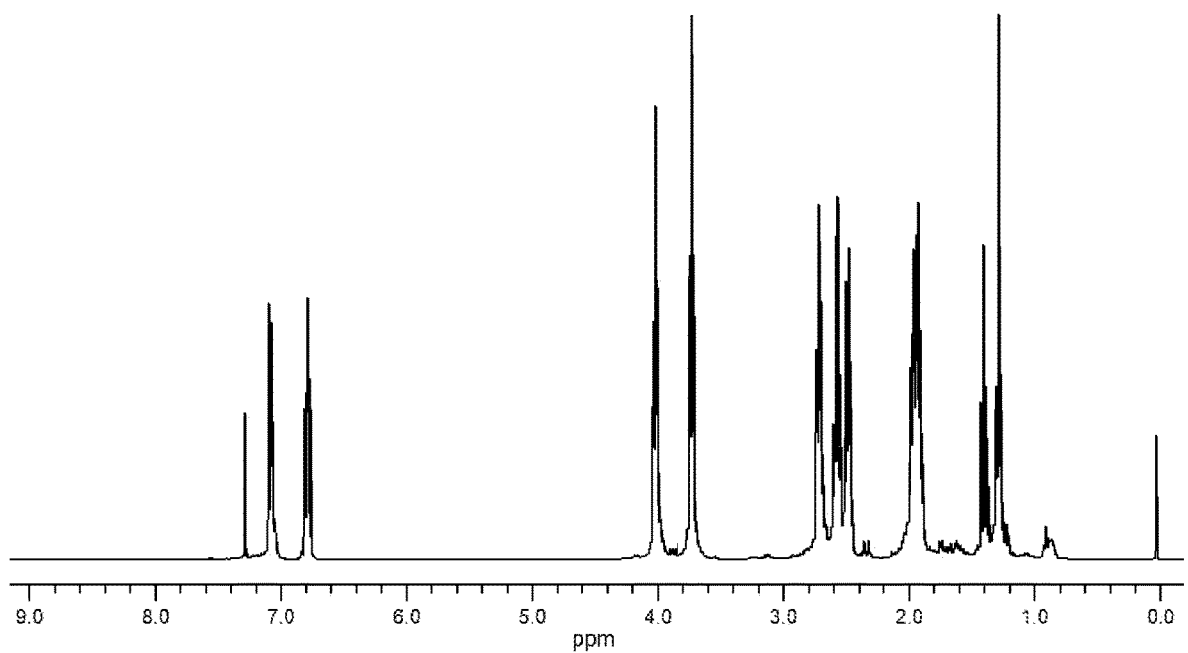
FIG. 3 is a $^1$H-NMR image of 5,5'-bis(3-mercaptopropyl)-2,2'-bis(3-mercaptopropoxy)-3,3'-dimethoxybiphenyl obtained in example 2.
Figure 4:
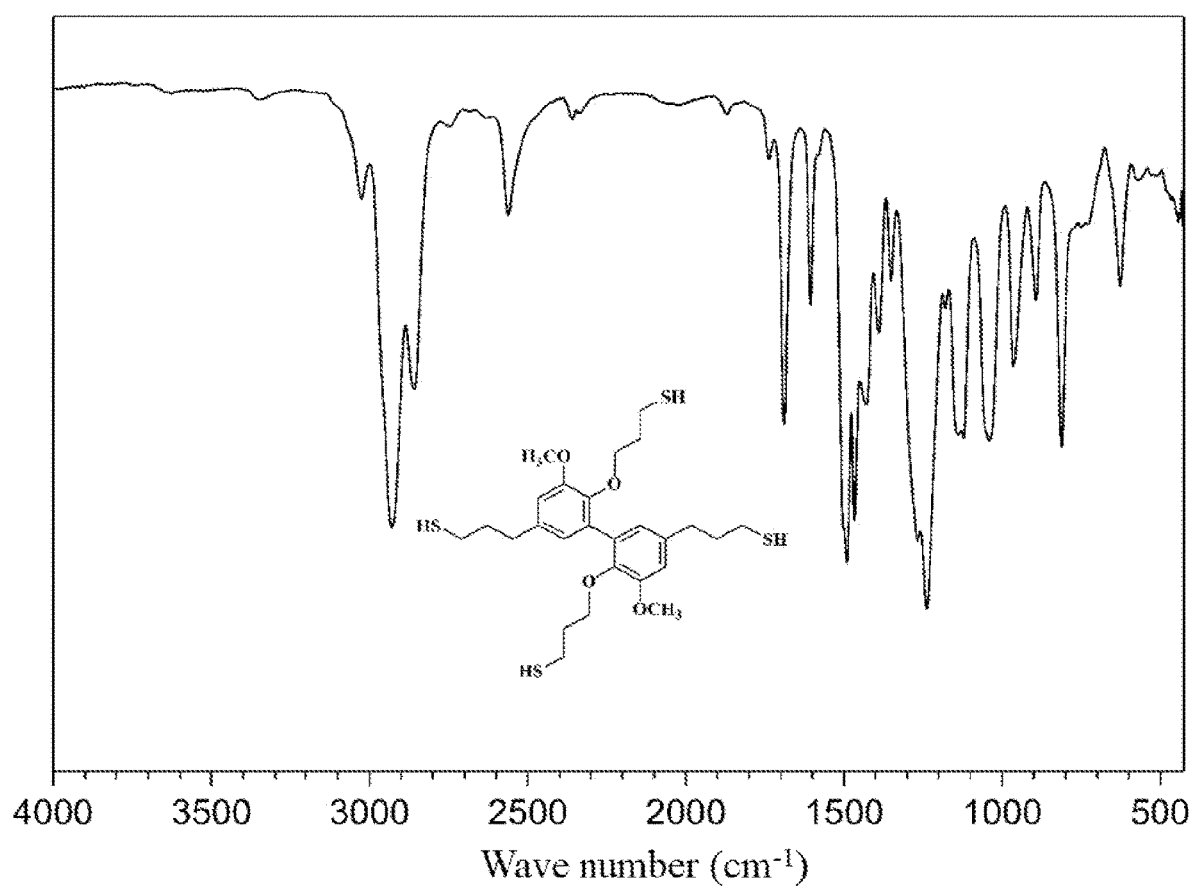
FIG. 4 is an IR spectrogram of 5,5'-bis(3-mercaptopropyl)-2,2'-bis(3-mercaptopropoxy)-3,3'-dimethoxybiphenyl obtained in example 2.

The $^1$H-NMR image and IR spectrogram of the 5,5'-bis(3-mercaptopropyl)-2,2'-bis(3-mercaptopropoxy)-3,3'-dimethoxybiphenyl are respectively shown in FIG. 3 and FIG. 4. It can be seen from FIG. 3 that proton peaks on the biphenyl ring are near chemical shifts 6.85 ppm and 7.05 ppm, peaks at chemical shifts 4.03 ppm, 2.59 ppm and 1.98 ppm correspond to the alkoxy groups on the biphenyl ring, peaks at chemical shifts 2.73 ppm, 2.49 ppm and 1.92 ppm correspond to the alkyl groups on the biphenyl ring, and peaks at chemical shifts 1.43 ppm and 1.31 ppm respectively correspond to the alkyl mercapto group and the alkoxy mercapto group on the biphenyl ring. It can be seen from FIG. 4 that an absorption peak on the biphenyl ring is at 1489 $cm^{-1}$, 818 $cm^{-1}$ corresponds to Ar—H bending vibration on the biphenyl ring, the C—H stretching vibration absorption peak on the alkyl chain is at 2925 $cm^{-1}$, the absorption peak occurring at 1242 $cm^{-1}$ is alkoxy C—O stretching vibration, and the absorption peak at 2560 $cm^{-1}$ corresponds to the mercapto group. Accordingly, the 5,5'-bis(3-mercaptopropyl)-2,2'-bis(3-mercaptopropoxy)-3,3'-dimethoxybiphenyl has a structure shown in formula (I), wherein, $R^1$, $R^2$, $R^5$ and $R^7$ are all hydrogen atoms, $R^3$ and $R^8$ are each independently selected from methoxy group, and $R^4$ and $R^6$ are both alkylene groups with 3 carbon atoms, and m and n are both 1.

Example 3

This example is used for illustrating the preparation of the polymercaptan compound (5,5'-bis(3-mercaptopropyl)-2,2'-bis(3-mercaptopentoxy)biphenyl) provided by the present disclosure, specifically comprising the following steps:

step 1: 80 g of magnolol was dissolved into 200 mL of acetone, 103.6 g of potassium carbonate and 7.9 g of phase transfer catalyst 18-crown-6 were added, the above mixture was heated to 70° C. under the protection of an inert gas and stirred for 20 min, then 98.3 g of 5-bromo-1-pentene was slowly added, the reaction solution was filtered after 8 h of reaction, the filtrate was distilled at reduced pressure to remove the solvent, washed with water three times and extracted with trichloromethane, and the organic phase was collected and evaporated to obtain a first intermediate product as a faint yellow liquid;

step 2: the first intermediate product obtained in step 1 was dissolved into 200 mL of tetrahydrofuran, 5.4 g of radical initiator azodiisobutyronitrile, the above mixture was heated to 70° C. under the protection of an inert gas, 96.2 g of thioacetic acid was slowly added, and the solvent and the excessive thioacetic acid were removed by distillation at reduced pressure after 12 h of reaction to obtain a second intermediate product as a faint yellow liquid;

step 3: the second intermediate product obtained in step 2 was dissolved into 300 mL of methanol, 60 mL of hydrochloric acid was added for hydrolysis, the above mixture was heated to 60° C. to be subjected to hydrolysis reaction for 12 h, the solvent was removed by distillation at reduced pressure, the product after distillation was washed with a 5% sodium dicarbonate solution twice and extracted with trichloromethane, and the organic phase was collected and evaporated to obtain 133.2 g of final product as a faint yellow thick liquid, i.e., 5,5'-bis(3-mercaptopropyl)-2,2'-bis(3-mercaptopentoxy) biphenyl, with a total yield of 82.4%. The 5,5'-bis(3-mercaptopropyl)-2,2'-bis(3-mercaptopentoxy) biphenyl substantially has no sulfur odor. By $^1$H-NMR and IR detection, it has a structure shown in formula (I), wherein, $R^1$, $R^2$, $R^3$, $R^5$, $R^7$ and $R^8$ are all hydrogen atoms, $R^4$ and $R^6$ are both alkylene groups with 3 carbon atoms, and m and n are both 3.

Example 4

This example is used for illustrating the preparation of the polymercaptan compound (5,5'-bis(3-mercaptopropyl)-2,2'-bis(3-mercaptopropoxy)biphenyl) provided by the present disclosure, specifically comprising the following steps:

step 1: 80 g of magnolol was dissolved into 200 mL of acetone, 103.6 g of potassium carbonate and 7.9 g of phase transfer catalyst 18-crown-6 were added, the above mixture was heated to 50° C. under the protection of an inert gas and stirred for 60 min, then 79.8 g of allyl bromide was slowly added, the reaction solution was filtered after 12 h of reaction, the filtrate was distilled at reduced pressure to remove the solvent, washed with water three times and extracted with trichloromethane, and the organic phase was collected and evaporated to obtain a first intermediate product as a faint yellow liquid;

step 2: the first intermediate product obtained in step 1 was dissolved into 200 mL of tetrahydrofuran, 8.0 g of radical initiator benzoyl peroxide, the above mixture was heated to 80° C. under the protection of an inert gas, 96.2 g of thioacetic acid was slowly added, the solvent and the excessive thioacetic acid were removed by distillation at reduced pressure after 5 h of reaction to obtain a second intermediate product as a faint yellow liquid;

step 3: the second intermediate product obtained in step 2 was dissolved into 300 mL of methanol, 60 mL of hydrochloric acid was added for hydrolysis, the above mixture was heated to 60° C. to be subjected to hydrolysis reaction for 12 h, the solvent was removed by distillation at reduced pressure, the product after distillation was washed with a 5% sodium dicarbonate solution twice and extracted with trichloromethane, and the organic phase was collected and evaporated to obtain 120.9 g of final product as a faint yellow thick liquid, i.e., 5,5'-bis(3-mercaptopropyl)-2,2'-bis(3-mercaptopropoxy)biphenyl, with a total yield of 83.5%. The 5,5'-bis(3-mercaptopropyl)-2,2'-bis(3-mercaptopropoxy)biphenyl substantially has no sulfur odor. By $^1$H-NMR and IR detection, it has a structure shown in formula (I), wherein, $R^1$, $R^2$, $R^3$, $R^5$, $R^7$ and $R^8$ are all hydrogen atoms, $R^4$ and $R^6$ are both alkylene groups with 3 carbon atoms, and m and n are both 1.

Example 5

This example is used for illustrating the preparation of the polymercaptan compound (5,5'-bis(3-mercaptopropyl)-2,2'-bis(3-mercaptopropoxy)biphenyl) provided by the present disclosure, specifically comprising the following steps:

step 1: 80 g of magnolol was dissolved into 200 mL of dimethylformamide, 42.1 g of potassium hydroxide and 9.67 g of phase transfer catalyst tetrabutyl ammonium bromide were added, the above mixture was heated to 100° C. under the protection of an inert gas and stirred for 10 min, then 50.5 g of allyl chloride was slowly added, the reaction solution was filtered after 4 h of reaction, the filtrate was distilled at reduced pressure to remove the solvent, washed with water three times and extracted with trichloromethane, and the organic phase was collected and evaporated to obtain a first intermediate product as a faint yellow liquid;

step 2: the first intermediate product obtained in step 1 was dissolved into 200 mL of tetrahydrofuran, 5.4 g of radical initiator azodiisobutyronitrile was added, the above mixture was heated to 50° C. under the protection of an inert gas, 89.3 g of thioacetic acid was slowly added, and the solvent and excessive thioacetic acid were removed by distilling at reduced pressure after reacting for 12 h to obtain a second intermediate product as a faint yellow liquid;

step 3: the second intermediate product obtained in step 2 was dissolved into 300 mL of methanol, 60 mL of hydrochloric acid was added for hydrolysis, the above mixture was heated to 70° C. to be subjected to hydrolysis reaction for 5 h, the solvent was removed by distillation at reduced pressure, the product after distillation was washed with a 5% sodium dicarbonate solution twice and extracted with trichloromethane, and the organic phase was collected and evaporated to obtain 111.6 g of final product as a faint yellow thick liquid, i.e., 5,5'-bis(3-mercaptopropyl)-2,2'-bis(3-mercaptopropoxy)biphenyl, with a total yield of 77.1%. The 5,5'-bis(3-mercaptopropyl)-2,2'-bis(3-mercaptopropoxy) biphenyl substantially has no sulfur odor. By 1H-NMR and IR detection, it has a structure shown in formula (I), wherein, $R^1$, $R^2$, $R^3$, $R^5$, $R^7$ and $R^8$ are all hydrogen atoms, $R^4$ and $R^6$ are both alkylene groups with 3 carbon atoms, and m and n are both 1.

Example 6

This example is used for illustrating the preparation of the thermosetting resin composition provided by the present disclosure. The resin composition comprises the following components in parts by weight: 50 parts of bisphenol A epoxy resin, 10 parts of hydrogenated bisphenol A epoxy resin, 38 parts of polymercaptan curing agent 5,5'-bis(3-mercaptopropyl)-2,2'-bis(3-mercaptopropoxy)biphenyl prepared in example 1, 3 parts of latent curing accelerator and 0.5 part of stabilizer triethyl borate.

After being weighed on a container, the above raw materials were sufficiently and evenly mixed using a dispersing device at room temperature or low temperature and then defoamed, and the resin composition was obtained after discharging and encapsulation.

Example 7

This example is used for illustrating the preparation of a thermosetting resin composition provided by the present disclosure. The resin composition comprises the following components in parts by weight: 50 parts of bisphenol A epoxy resin, 10 parts of hydrogenated bisphenol A epoxy resin, 42 parts of polymercaptan curing agent 5,5'-bis(3-mercaptopropyl)-2,2'-bis(3-mercaptopropoxy)-3,3'-dimethoxybiphenyl prepared in example 2, 3 parts of latent curing accelerator and 0.5 part of stabilizer triethyl borate.

After being weighed on a container, the above raw materials were sufficiently and evenly mixed using a dispersing device at room temperature or low temperature and then defoamed, and the resin composition was obtained after discharging and encapsulation.

Example 8

This example is used for illustrating the preparation of the UV curing resin composition provided by the present disclosure. The resin composition comprises the following components in parts by weight: 50 parts of bisphenol A epoxy diacrylate, 10 parts of tricyclodecane dimethanol diacrylate, 32 parts of polymercaptan curing agent 5,5'-bis(3-mercaptopropyl)-2,2'-bis(3-mercaptopropoxy)biphenyl prepared in example 1, 3 parts of photoinitiator 2,2-dimethoxy-2-phenyl acetophenone and 0.2 part of polymerization inhibitor p-hydroxyanisole.

After being weighed on a container, the above raw materials were sufficiently and evenly mixed using a dispersing device at room temperature or low temperature at dark and then defoamed, and the resin composition was obtained after discharging and encapsulation.

Example 9

This example is used for illustrating the preparation of the UV curing resin composition provided by the present disclosure. The resin composition comprises the following components in parts by weight: 50 parts of bisphenol A epoxy diacrylate, 10 parts of tricyclodecane dimethanol diacrylate, 36 parts of polymercaptan curing agent 5,5'-bis(3-mercaptopropyl)-2,2'-bis(3-mercaptopropoxy)-3,3'-dimethoxybiphenyl prepared in example 2, 3 parts of photoinitiator 2,2-dimethoxy-2-phenyl acetophenone and 0.2 part of polymerization inhibitor p-hydroxyanisole.

After being weighed on a container, the above raw materials were sufficiently and evenly mixed using a dispersing device at room temperature or low temperature at dark and then defoamed, and the resin composition was obtained after discharging and encapsulation.

Example 10

This example is used for illustrating the preparation of the UV/thermal curing composition provided by the present disclosure. The resin composition comprises the following components in parts by weight: 25 parts of bisphenol A epoxy resin, 5 parts of hydrogenated bisphenol A epoxy resin, 25 parts of bisphenol A epoxy diacrylate, 5 parts of tricyclodecane dimethanol diacrylate, 35 parts of polymercaptan curing agent 5,5'-bis(3-mercaptopropyl)-2,2'-bis(3-mercaptopropoxy)biphenyl prepared in example 1, 1 part of photoinitiator 2-hydroxy-2-methylpropiophenone and 1 part of diphenyl-(2,4,6-trimethylbenzoyl)phosphine oxide, 2 parts of latent curing accelerator, 0.3 part of stabilizer triethyl borate and 0.1 part of polymerization inhibitor p-hydroxyanisole.

After being weighed on a container, the above raw materials were sufficiently and evenly mixed using a dispersing device at room temperature or low temperature at dark and then defoamed, and the resin composition was obtained after discharging and encapsulation.

Example 11

This example is used for illustrating the preparation of the UV/thermal curing composition provided by the present disclosure. The resin composition comprises the following components in parts by weight: 25 parts of bisphenol A epoxy resin, 5 parts of hydrogenated bisphenol A epoxy resin, 25 parts of bisphenol A epoxy diacrylate, 5 parts of tricyclodecanedimethanol diacrylate, 39 parts of polymercaptan curing agent 5,5'-bis(3-mercaptopropyl)-2,2'-bis(3-mercaptopropoxy)-33'-dimethoxybiphenyl prepared in example 2, 1 part of photoinitiator 2-hydroxy-2-methylpropiophenone and 1 part of diphenyl-(2,4,6-trimethylbenzoyl)phosphine oxide, 2 parts of latent curing accelerator, 0.3 part of stabilizer triethyl borate and 0.1 part of polymerization inhibitor p-hydroxyanisole.

After being weighed on a container, the above raw materials were sufficiently and evenly mixed using a dispersing device at room temperature or low temperature at dark and then defoamed, and the resin composition was obtained after discharging and encapsulation.

Comparative Example 1

The thermosetting resin composition was prepared following the method in example 6 except that the polymercaptan curing agent 5,5'-bis(3-mercaptopropyl)-2,2'-bis(3-mercaptopropoxy)biphenyl prepared in example 6 was replaced with the polymercaptan curing agent pentaerythritol tetra(3-mercaptopropionate) having the same mercaptan functional group equivalent and containing an ester bond, and the rest conditions were the same as those in example 6, so that the thermosetting resin composition was obtained.

Comparative Example 2

The thermosetting resin composition was prepared following the method in example 6 except that the polymercaptan curing agent 5,5'-bis(3-mercaptopropyl)-2,2'-bis(3-mercaptopropoxy)biphenyl prepared in example 6 was replaced with 1,3,4,6-tetra(2-mercaptoethyl) glycolurea having the same mercaptan functional group equivalent, and the rest conditions were the same as those in example 6, so that the thermosetting resin composition was obtained.

Comparative Example 3

The thermosetting resin composition was prepared following the method in example 6 except that the polymercaptan curing agent 5,5'-bis(3-mercaptopropyl)-2,2'-bis(3-mercaptopropoxy)biphenyl prepared in example 6 was replaced with a glycyl urea derivatives complex (the glycyl urea derivatives complex is a mixture of 1,3,4,6-tetra(2-mercaptoethyl) glycylurea and 1,1-(dithiodiethylene diyl)-bis[3,4,6-tri(2-mercaptoethyl)glycylurea] and wherein the mass percent of 1,1-(dithiodiethylene diyl)-bis[3,4,6-tri(2-mercaptoethyl)glycylurea] is 8%) having the same mercaptan functional group equivalent, and the rest conditions were the same as those in example 6, so that the thermosetting resin composition was obtained.

Comparative Example 4

The UV curing resin composition was prepared following the method in example 8 except that the polymercaptan curing agent 5,5'-bis(3-mercaptopropyl)-2,2'-bis(3-mercaptopropoxy)biphenyl prepared in example 8 was replaced with pentaerythritol tetra(3-mercaptopropionate) having the same mercaptan functional group equivalent and containing an ester bond, and the rest conditions were the same as those in example 8, so that the UV curing resin composition was obtained.

Comparative Example 5

The UV curing resin composition was prepared following the method in example 8 except that the polymercaptan curing agent 5,5'-bis(3-mercaptopropyl)-2,2'-bis(3-mercaptopropoxy)biphenyl prepared in example 8 was replaced with 1,3,4,6-tetra(2-mercaptoethyl) glycolurea having the same mercaptan functional group equivalent, and the rest conditions were the same as those in example 8, so that the UV curing resin composition was obtained.

Comparative Example 6

The UV curing resin composition was prepared following the method in example 8 except that the polymercaptan curing agent 5,5'-bis(3-mercaptopropyl)-2,2'-bis(3-mercaptopropoxy)biphenyl prepared in example 8 was replaced with a glycylurea complex (the glycylurea complex is a mixture of 1,3,4,6-tetra(2-mercaptoethyl)glycylurea and 1,1-(dithiodiethylene diyl)-bis[3,4,6-tri(2-mercaptoethyl) glycylurea] and wherein the mass percent of 1,1-(dithiodiethylene diyl)-bis[3,4,6-tri(2-mercaptoethyl) glycylurea] is 8%) having the same mercaptan functional group equivalent, and the rest conditions were the same as those in example 8, so that the UV curing resin composition was obtained.

Comparative Example 7

The UV/thermal dual-curing resin composition was prepared following the method in example 10 except that the polymercaptan curing agent 5,5'-bis(3-mercaptopropyl)-2, 2'-bis(3-mercaptopropoxy)biphenyl prepared in example 10 was replaced with the polymercaptan curing agent pentaerythritol tetra(3-mercaptopropionate) having the same mercaptan functional group equivalent and containing an ester bond, and the rest conditions were the same as those in example 10, so that the UV/thermal dual-curing resin composition was obtained.

Comparative Example 8

The UV/thermal dual-curing resin composition was prepared following the method in example 10 except that the polymercaptan curing agent 5,5'-bis(3-mercaptopropyl)-2, 2'-bis(3-mercaptopropoxy)biphenyl prepared in example 10 was replaced with 1,3,4,6-tetra(2-mercaptoethyl)glycolurea having the same mercaptan functional group equivalent, and the rest conditions were the same as those in example 10, so that the UV/thermal dual-curing resin composition was obtained.

Comparative Example 9

The UV/thermal dual-curing resin composition was prepared following the method in example 10 except that the polymercaptan curing agent 5,5'-bis(3-mercaptopropyl)-2, 2'-bis(3-mercaptopropoxy)biphenyl prepared in example 10 was replaced with a glycylurea complex (the glycylurea complex is a mixture of 1,3,4,6-tetra(2-mercaptoethyl) glycylurea and 1,1-(dithiodiethylene diyl)-bis[3,4,6-tri(2-mercaptoethyl)glycylurea] and wherein the mass percent of 1,1-(dithiodiethylene diyl)-bis[3,4,6-tri(2-mercaptoethyl) glycylurea] is 8%) having the same mercaptan functional group equivalent, and the rest conditions were the same as those in example 10, so that the UV/thermal dual-curing resin composition was obtained.

Test Example (1) Crystal precipitation time (h): time starting from completion of preparation of resin compositions to identification of crystal precipitation after the resin compositions prepared in examples and comparative examples were respectively placed at room temperature. It was noted that identification of crystal precipitation was visually performed, and the longest test time was 240 h.
(2) Curing conditions: the resin compositions prepared in examples 6-7 and comparative examples 1-3 underwent heat curing for 60 min in an oven at 80° C. to obtain samples after curing; the resin compositions prepared in examples 8-9 and comparative examples 4-6 were irradiated and cured for 10 s using an UV light source (365 nm, light intensity 1000 mW/cm$^2$) to obtain samples after curing; the resin compositions prepared in examples 10-11 and comparative examples 7-9 were irradiated and cured for 4 s using the UV light source (365 nm, light intensity 1000 mW/cm$^2$) and then underwent heat curing for 60 min in an oven at 80° C. to obtain samples after curing.
(3) Glass transition temperature (° C.): test was performed by using a Q-800 dynamic thermal mechanical analysis tester (DMA) of an American TA instrument, and the resin compositions prepared in examples and comparative examples as described above were completely cured and then prepared into slices with a size of 42 mm×8 mm×0.3 mm, the change rule of loss factor (tan δ) with temperatures was measured within the temperature range of −40 to 250° C. at the atmosphere of a liquid nitrogen and under a film stretching mode, wherein the heating rate was 10° C./min and the test frequency was 10 Hz, so as to determine the glass transition temperature Tg (° C.) of the cured resin composition.
(4) Hot bonding strength (MPa): the resin compositions prepared in samples and comparative examples as described above were respectively coated onto different stainless steel sheets, overlapped and laminated with tempered glass sheets to manufacture test samples with a bonding area being 25.4 mm×5 mm, and the thickness of an adhesive layer being ensured to 0.1 mm, the test examples were respectively cured, then two sheets of the completely cured samples were stretched in an opposite direction using a universal testing machine and then tested at an ambient temperature of 85° C., the tested force values were recorded in strength (MPa); the samples after curing were treated under the heating and humidifying conditions of 85° C./85% RH/120 h, and then the shearing bonding strengths (MPa) of the samples were tested again at the ambient temperature of 85° C. and recorded.

The test results of the above-mentioned crystal precipitation time, glass transition temperature and hot bonding strength before and after heating and humidifying are seen in Table 1 below.

TABLE 1

| Item | Crystal precipitation time (h) | Tg (° C.) | Hot bonding strength after just sample preparation (MPa) | Hot bonding strength after heating and humidifying (MPa) |
| --- | --- | --- | --- | --- |
| Example 6 | >240 | 123 | 8.97 | 8.01 |
| Example 7 | >240 | 122 | 9.05 | 8.13 |
| Example 8 | >240 | 128 | 6.52 | 5.87 |
| Example 9 | >240 | 126 | 6.83 | 6.14 |
| Example 10 | >240 | 125 | 7.10 | 6.39 |
| Example 11 | >240 | 124 | 7.15 | 6.41 |
| Comparative example 1 | >240 | 63 | 5.45 | 0.80 |
| Comparative example 2 | 6.5 | 115 | 7.76 | 6.58 |
| Comparative example 3 | >240 | 112 | 8.32 | 6.97 |
| Comparative example 4 | >240 | 67 | 4.68 | 0.69 |
| Comparative example 5 | 26 | 117 | 5.94 | 4.92 |
| Comparative example 6 | >240 | 115 | 6.45 | 5.45 |
| Comparative example 7 | >240 | 65 | 5.05 | 0.72 |
| Comparative example 8 | 13 | 116 | 6.63 | 5.63 |
| Comparative example 9 | >240 | 113 | 7.06 | 5.95 |

In combination with Table 1, examples 1-11 and/or comparative examples 1-9 are analyzed and compared. First, it can be seen from analysis of examples 1-5 that the polymercaptan compound of the present disclosure is of a liquid, free of an ester bond, has high yield and substantially has no byproducts, is simple in preparation process, and can effectively reduce cost; by comparative analysis between example 6 and comparative examples 1-3, example 8 and comparative examples 4-6, example 10 and comparative examples 7-9, it can be seen that the resin composition prepared by using the polymercaptan compound of the present disclosure as the curing agent has more excellent and obvious advantages in the aspects of crystal precipitation time, glass transition temperature and hot bonding strength before and after heating and humidifying, indicating that the resin composition prepared in the present disclosure has better stability (long crystal precipitation time), higher heat resistance (high glass transition temperature and high hot bonding strength), more excellent bonding property and better hygrothermal hydrolysis resistance.

It can be seen from comparison of example 6, example 8 and example 10 with comparative example 1, comparative example 4 and comparative example 7 that after the polymercaptan compound of the present disclosure is replaced with the polymercaptan curing agent pentaerythritol tetra(3-mercaptopropionate) containing the ester bond, the glass transition temperatures of the resin compositions after curing are all sharply decreased, and meanwhile the hot bonding strengths are also obviously decreased, particularly hot bonding strengths after heating and humidifying are almost exhausted, indicating that the polymercaptan compound of the present disclosure has a significant effect on heat resistance, bonding property and hygrothermal hydrolysis resistance of the resin composition.

It can be seen from comparison of example 6, example 8 and example 10 with comparative examples 2-3, comparative examples 5-6 and comparative examples 8-9 that in example 2, comparative example 5 and comparative example 8, after the polymercaptan compound of the present disclosure is replaced with 1,3,4,6-tetra(2-mercaptoethyl) glycolurea, the crystal precipitation time of the resin composition is greatly shortened to 6.5 h, 26 h and 13 h and meanwhile the glass transition temperature and hot bonding strength of the cured product are also reduced to a certain extent, indicating that since the solid polymercaptan curing agent 1,3,4,6-tetra(2-mercaptoethyl)glycolurea leads to the reduction in the comprehensive performance of the resin composition is reduced due to the easy crystal precipitation of the solid polymercaptan curing agent 1,3,4,6-tetra(2-mercaptoethyl)glycolurea; in comparative example 3, comparative example 6 and comparative example 9, the problem of short crystal precipitation time of the polymercaptan curing agent 1,3,4,6-tetra(2-mercaptoethyl)glycolurea was improved by adding a part of 1,1-(dithiodiethyl)-bis[3,4,6-tri(2-mercaptoethyl)glycolurea], however, this scheme obviously increases the cost, and at the same time the glass transition temperature and hot bonding strength of the resin composition are still slightly lower than those of the resin composition of the present disclosure, indicating that the polymercaptan compound of the present disclosure has a significant effect on heat resistance, bonding property and hygrothermal hydrolysis resistance under the conditions of low cost and no crystal precipitation.

To sum up, except for low odor, the polymercaptan compound of the present disclosure has no ester bond, good moisture resistance and heat resistance, is a liquid at room temperature, and can be directly used as the curing agent for the synthesis of the resin composition. The resin composition can be used as the ingredient of the sealant and the adhesive. Compared with the combination of two mercaptoethyl glycourea compounds proposed in patent CN201680014880.5 as the ingredient of the curing agent, the polymercaptan compound of the present disclosure is simple in reaction process without additional coupling to form the oligomer mixture and combination with other polymercaptan compounds, and is low in cost. In addition, the polymercaptan compound provided by the present disclosure can reduce the storage stability risk of the single-component low-temperature curing epoxy resin, is long in working life and is wide in application prospect.

Although the embodiments of the present disclosure have been illustrated and described above, it should be understood that without departing from the principle and purposes of the present disclosure, variations, modifications, replacements and deformations can be made by those skilled in the art within the scope of the present disclosure.

What is claimed is:
1. A polymercaptan compound, which is represented by formula (I):

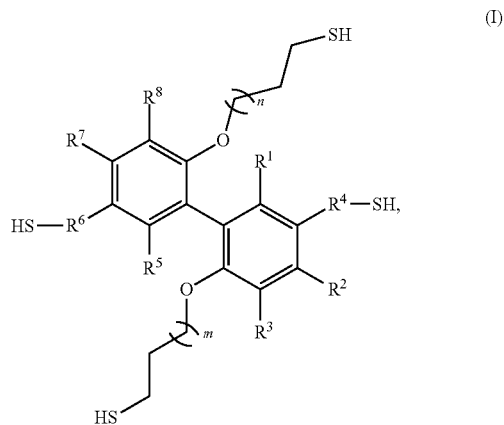

in the formula (I), $R^1$, $R^2$, $R^3$, $R^5$, $R^7$ and $R^8$ are each independently selected from one of a hydrogen atom, an alkyl group with 1-5 carbon atoms and an alkoxy group with 1-5 carbon atoms, $R^4$ and $R^6$ are each independently selected from an alkylene group with 1-5 carbon atoms, and m and n are each independently 0, 1, 2 or 3.

2. The polymercaptan compound according to claim 1, wherein in the formula (I), $R^1$, $R^2$, $R^5$ and $R^7$ are all hydrogen atoms, $R^3$ and $R^8$ are each independently selected from a hydrogen atom or a methoxy group, $R^4$ and $R^6$ are each independently selected from an alkylene group with 3-5 carbon atoms, and m and n are 1.

3. The polymercaptan compound according to claim 1, wherein the polymercaptan compound is selected from at least one of 5,5'-bis(3-mercaptopropyl)-2,2'-bis(3-mercaptobutoxy)biphenyl, 5,5'-bis(3-mercaptopropyl)-2,2'-bis(3-mercaptobutoxy)-3,3'-dimethoxybiphenyl, 5,5'-bis(3-mercaptopropyl)-2,2'-bis(3-mercaptopentoxy)biphenyl, 5,5'-bis(3-mercaptopropyl)-2,2'-bis(3-mercaptopentoxy)-3,3'-dimethoxybiphenyl, 5,5'-bis(3-mercaptopropyl)-2,2'-bis(3-mercaptopropoxy)biphenyl and 5,5'-bis(3-mercaptopropyl)-2,2'-bis(3-mercaptopropoxy)-3,3'-dimethoxybiphenyl.

4. A method for preparing the polymercaptan compound according to claim 1, the method comprising the following steps:
   step 1: performing substitution reaction on a phenol compound represented by formula (II) and a first compound represented by formula (III) in the presence of a phase transfer catalyst and under an alkaline condition, and purifying to obtain a first intermediate product as a colorless or faint yellow liquid;
   step 2: performing radical addition reaction on the first intermediate product and thioacetic acid in the presence of a radical initiator, and purifying to obtain a second intermediate product as a colorless or faint yellow liquid;
   step 3: performing hydrolysis reaction on the second intermediate, and purifying to obtain a product as a colorless or faint yellow thick liquid, i.e., the polymercaptan compound;

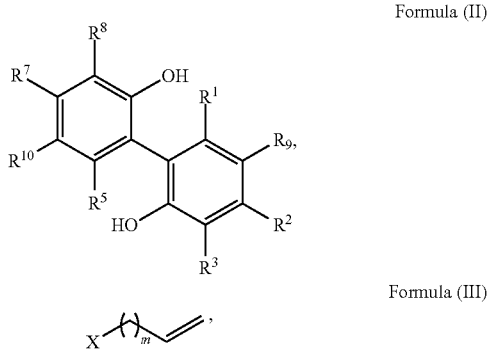

in the formula (II), $R^1$, $R^2$, $R^3$, $R^5$, $R^7$ and $R^8$ are each independently selected from one of a hydrogen atom, a lower alkyl group with 1-5 carbon atoms and an alkoxy group with 1-5 carbon atoms, and $R^9$ and $R^{10}$ are each independently selected from a 1-alkenylalkyl group with 3-5 carbon atoms;

in the formula (III), X represents chlorine or bromine, and m is 0, 1, 2 or 3.

5. The method for preparing the polymercaptan compound according to claim 4, wherein in step 1, the substitution reaction is that the phenol compound represented by formula (II) is dissolved into an organic solvent, an alkali is added to provide an alkaline condition, the phase transfer catalyst is added, then above mixture is heated to 40-100° C. under the protection of an inert gas and stirred for 10-60 min, subsequently the first compound represented by formula (III) is added to react for 4-12 h, then a reaction solution is filtered, filtrate is distilled at reduced pressure to remove a solvent, washed with water three times and extracted with trichloromethane, and an organic phase is collected and evaporated to obtain the first intermediate product as the colorless or faint yellow liquid.

6. The method for preparing the polymercaptan compound according to claim 4, wherein in step 2, the radical addition reaction is that the first intermediate product is dissolved into an organic solvent, the radical initiator is added, above mixture is heated to 40-100° C. under the protection of an inert gas, thioacetic acid is slowly added to perform radical addition reaction for 4-12 h, and then the solvent is removed by distilling at reduced pressure to obtain the second intermediate product as the colorless or faint yellow liquid.

7. The method for preparing the polymercaptan compound according to claim 4, wherein in step 3, the hydrolysis reaction is that the second intermediate product was dissolved into an organic solvent, hydrochloric acid or sodium hydroxide is added, above mixture is heated to 50-100° C. to react for 3-12 h, the solvent is removed by distilling at reduced pressure, a product obtained after distillation is washed with a 2-8% sodium bicarbonate solution twice and extracted with trichloromethane, and organic phase is collected and then evaporated to obtain the product as the colorless or faint yellow thick liquid, i.e., the polymercaptan compound.

8. A curing agent, which at least comprises the polymercaptan compound according to claim 1.

9. A resin composition, which at least comprises the curing agent according to claim 8, and a resin which is an alkene compound and/or epoxy resin having a carbon-carbon double bond in a molecule.

10. The resin composition according to claim 9, wherein when the resin is the epoxy resin, the resin composition comprises an amine as a curing accelerator.

11. The resin composition according to claim 9, wherein when the resin is the epoxy resin, the resin composition comprises a reaction product of the epoxy resin and an amine as a curing accelerator.

12. The resin composition according to claim 9, wherein when the resin is the epoxy resin, the resin composition comprises a reaction product of a compound having one or more isocyanate groups in a molecule and a compound having at least one of primary amino and secondary amino as a curing accelerator.

13. An adhesive or a sealant comprising the resin composition according to claim 9 as an ingredient of an adhesive or a sealant.

* * * * *